United States Patent [19]

Angelsen

[11] Patent Number: 4,893,628

[45] **Date of Patent: * Jan. 16, 1990**

[54] DUAL ELEMENT ULTRASONIC TRANSDUCER PROBE FOR COMBINED IMAGING OF TISSUE STRUCTURES AND BLOOD FLOW IN REAL TIME

[76] Inventor: Bjørn Angelsen, Dept. of Biomedical Eng., University of Trondheim, Trondheim-Rit, Norway, N 7006

[ * ] Notice: The portion of the term of this patent subsequent to Jul. 19, 2005 has been disclaimed.

[21] Appl. No.: 176,881

[22] Filed: Apr. 4, 1988

[51] Int. Cl.[4] .................................... A61B 8/00

[52] U.S. Cl. .................... 128/660.05; 128/660.09; 73/633

[58] Field of Search .................. 128/660.05, 660.09, 128/660.10, 662.04; 73/625-633, 861.25

[56] References Cited

U.S. PATENT DOCUMENTS

| | | | |
|---|---|---|---|
| 4,228,687 | 10/1980 | Fraser | 128/660.09 X |
| 4,649,925 | 3/1987 | Dow et al. | 128/660.1 |
| 4,757,818 | 7/1988 | Angelsen | 128/662.04 X |

FOREIGN PATENT DOCUMENTS

| | | | |
|---|---|---|---|
| 2941865 | 5/1981 | Fed. Rep. of Germany | 128/660.09 |
| 2027197 | 2/1980 | United Kingdom | 128/660.09 |

*Primary Examiner*—Francis Jaworski

*Attorney, Agent, or Firm*—Cohen, Pontani & Lieberman

[57] ABSTRACT

An ultrasonic probe for use in combined and time shared ultrasonic imaging of biological tissue structures together with blood velocity measurements and imaging of blood flow based on the Doppler principle, in which rapid changes of sweep movements of the probe between the respective imaging and measurement modes of operation are performed, said probe having two mechanically steerable ultrasonic beams, comprising:

a linear motion electric drive motor having a stationary magnet means and a coil assembly which is linearly moveable with respect to said magnet means by the application of electric current to said coil assembly, two ultrasonic transducers for emitting respective ultrasonic beams and disposed to be pivotable around separate axes within separate angular sectors for sweeping the two ultrasonic beams within the two separate angular sectors, respectively, mechanical coupling assembly for connecting the linear drive motor to the pivotable transducer elements, converting the linear motion of the motor coil assembly into a limited rotary motion of the transducers within said angular sectors, said mechanical coupling assembly comprising at least three pulleys mounted at a distance from each other, and at least one flexible pulling element trained about and rotatably connecting said at least three pulleys with each other, said ultrasonic transducers being each rotatably connected to a separate one of the pulleys, and said motor coil assembly being mechanically connected to said at least one pulling element at a portion thereof lying between two pulleys of said at least three pulleys, whereby reciprocating linear movement of the coil assembly causes said angular sweeping of the transducer elements.

15 Claims, 4 Drawing Sheets

FIG. 1a
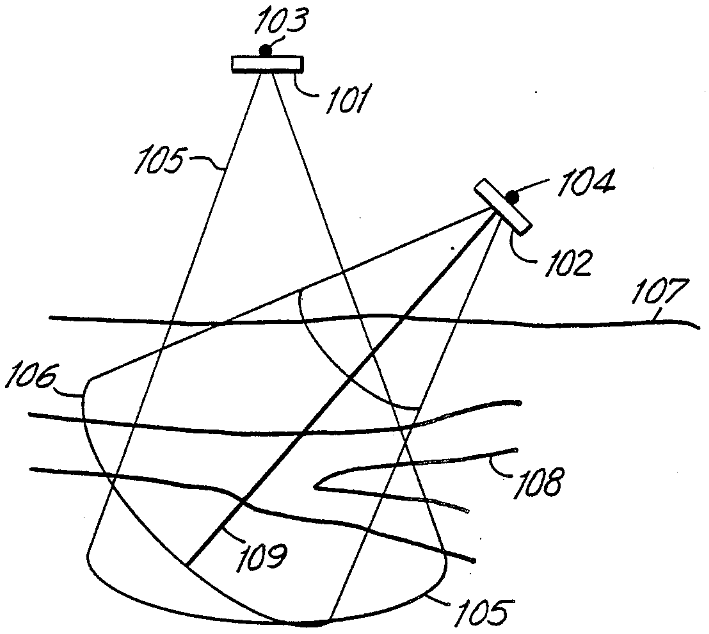
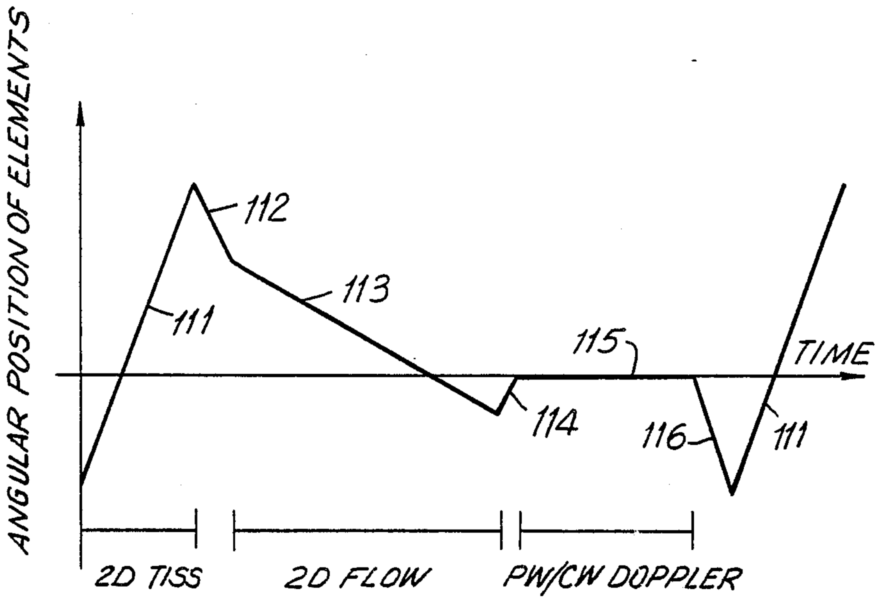
FIG. 1b

DUAL ELEMENT ULTRASONIC TRANSDUCER PROBE FOR COMBINED IMAGING OF TISSUE STRUCTURES AND BLOOD FLOW IN REAL TIME

BACKGROUND OF THE INVENTION

This invention relates to an ultrasonic transducer probe with two mechanically steered ultrasonic beams which can be steered within two overlapping sectors of a plane for combined imaging of tissue structures and blood flow. The probe is primarily intended to be used for ultrasonic imaging of biological tissue structures, such as peripheral and abdominal vessels, together with blood velocity measurements and imaging of blood flow therein. The advantage of having two ultrasonic beams is that they each can be directed towards the region of investigation with optimal directions for the purpose, one at approximately normal inclination to the artery to produce tissue imaging with maximum resolution of the arterial wall, the other at a pointed angle to the artery to obtain a component of the blood velocity vector along the beam to produce an acceptable Doppler shift of the backscattered ultrasound from the blood, for measurement of blood velocities and imaging of blood flow. Moreover, the use of separate ultrasonic transducers to generate the two beams makes it possible to select optimal ultrasonic frequencies for each purpose, as for example 10 MHz to generate the tissue image of arteries close to the skin, and 5 MHz for Doppler measurement of blood velocities in the artery.

An additional advantage of the present invention is that it uses a single motor for the drive of both elements, giving a compact design. The drive mechanism is efficient so that ultra-fast switching of the directions of the beams can be obtained, making it possible to do time-shared imaging and Doppler measurements at such a rate that they appear simultaneous to the user according to the principle described in B. A. J. Angelsen, K. Kristoffersen: "A method for combining Ultrasonic Doppler Measurement and Pulse Echo Amplitude Imaging", U.S. Pat. No. 4,559,952.

B. A. J. Angelsen, K. Kristoffersen: "Method and Apparatus for Generating a Multidimensional Map of Blood Velocities using Backscattered Ultrasound and the Doppler Effect", U.S. patent application. Ser. No. 603,511 filed Apr. 24, 1984.

For the design we would also reference

B. A. J. Angelsen: "An Ultrasonic Transducer Probe with a Mechanically Steerable Beam", U.S. Pat. No. 4,757,818.

There exist in the marketplace several devices that do imaging of tissue structures and blood flow from the same acoustic transducer element(s) based on a compromise of the beam direction required for the two modes of imaging. Thus the novelty of the present invention lies in the mechanical design by which two separate transducer elements with different beam directions can be used, together with a compact and efficient design using a single drive motor so that such a rapid acceleration of the beam direction can be achieved to obtain complex sweep sequences like for instance the one in FIG. 1 to be described further below. It is also important, especially for flow imaging, that the beam motion is smooth in the sweep intervals to avoid high Doppler shifts from tissue.

The rapid switching of the beam direction is necessary to obtain a time shared imaging and Doppler measurement of the blood velocities using the Missing Signal Estimator technique, according to B. A. J. Angelsen, K. Kristoffersen: "Method and Apparatus for Synthesizing a Continuous Estimate signal from Segments of a Gaussian Signal Provided by Ultrasonic Doppler Measurement on a Fluid Flow", U.S. patent application Ser. No. 606,277 (Cont. 903,826), The missing signal estimator is used to generate a Doppler substitute signal based on the Doppler measurements in the intervals when the transducer stands still, which substitutes the Doppler signal in the periods when 2D tissue or flow imaging is done, so that an apparent simultaneous imaging and Doppler measurement is obtained.

According to this invention the above is obtained by providing an ultrasonic probe for use in combined and time shared ultrasonic imaging of biological tissue structures together with blood velocity measurements and imaging of blood flow based on the Doppler principle, in which rapid changes of sweep movements of the beams between the respective imaging and measurement modes of operation are performed, said probe having at least two mechanically steerable ultrasonic beams, comprising:

a linear motion electric drive motor having a stationary magnet means and a coil assembly which is linearly moveable with respect to said magnet means by the application of electric current to said coil assembly, at least two ultrasonic transducer elements for emitting respective ultrasonic beams and disposed to be pivotable about separate axes within separate angular sectors for sweeping the two ultrasonic beams within the two separate angular sectors, respectively, mechanical coupling means for connecting the linear drive motor to the pivotable transducer elements, and converting the linear motion of the motor coil assembly into a limited rotary motion of the transducer elements within said angular sectors, said mechanical coupling means comprising at least three pulleys mounted at a distance from each other, and at least one flexible pulling element trained about and rotatably connecting said at least three pulleys with each other, said ultrasonic transducer elements being each rotatably connected to a separate one of the pulleys, and said motor coil assembly being mechanically connected to said at least one pulling element at a portion thereof lying between two pulleys of said at least three pulleys, whereby reciprocating linear movement of the coil assembly causes said angular sweeping of the transducer elements.

SUMMARY OF THE DRAWINGS

The invention, together with additional novel features and advantages thereof, shall be described more in detail below with reference to the drawings, in which:

FIG. 1 shows in diagrams 1*a* and 1*b* an example of a composite angular sweep of the two ultrasonic transducer assemblies with fast jumps in beam direction for combined tissue imaging, flow imaging and blood velocity measurements;

DETAILED DESCRIPTION OF THE INVENTION

Figure 2A:
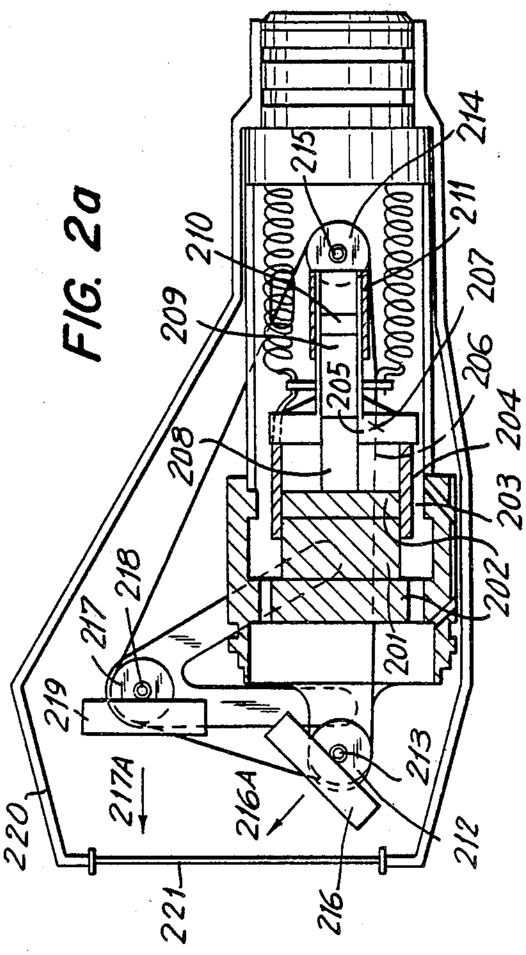
FIGS. 2*a* and 2*b* show simplified longitudinal sections of the preferred embodiment of a probe according to this invention.

FIG. 1*a* illustrates two acoustic transducer elements, 101 and 102, respectively pivoting around the centers 103 and 104 so that the beams from the elements are swept in two overlapping sectors of the plane, 105 and 106. The figure illustrates a typical measurement situation where the beams cross the skin 107 and are directed at a vessel 108. Element 101 is used for imaging of tissue structures like the vessel walls, generating a beam which can be swept within a sector 105 so that the beam is approximately normal to the vessel wall for maximum resolution of the wall, and element 102 is used for Doppler measurement of blood velocity and imaging of blood flow, generating a beam which is swept within a sector 106 so that the beam has a pointed angle to the direction of blood flow to obtain a Doppler shift of the backscattered signal from the flowing blood. For measurement of blood velocities along a defined beam direction, element 102 can be stopped at an arbitrary direction within its sweeping sector, indicated by a line 109. According to the invention, the two elements move together driven by the same motor, but they are used in timed sequence for their different purpose. FIG. 1*b* shows an example of a typical time variation of the angular position of the beams. The curve indicates the angle of each beam relative to the center direction of its sector. Thus, there is included:

(1) a sector sweep 111 of the beam to do a pulse echo amplitude imaging of biological tissue (~20 msec) using element 101;

(2) a quick change of beam direction 112 (~5 msec or less) to do another sector sweep 113 of smaller opening angle for pulse echo Doppler flow imaging (~40 msec) using element 102;

(3) another quick change of beam direction 114 (~5 msec or less) to go to a stationary direction 115 to do either pulsed or continuous wave Doppler blood velocity measurements using element 102;

(4) another quick change of beam direction 116 to start a new sequence of sweeps 111–115.

For the design of the probe the following requirements are set:

(i) fast acceleration of the beam directions to provide short switching time (112, 114, 116) between modes of operation (2D structure imaging, 2D flow imaging, Doppler blood velocity measurements); and (ii) constant sweep velocity of the beam (i.e. no high frequency vibrations) to avoid high Doppler shifts of signals from tissue, and thereby artifacts in the flow image.

For point (ii) it is important to avoid any sort of gear transmission, like bevel gear, rack and pinion etc., because these can cause vibrations if not carefully manufactured, which will introduce a cost problem. It is therefore preferred to use either a drive motor where the acoustic transducer is directed mounted to the moving part of the motor (being either part of this or connected for instance through a rod), or a pulley system or belt type of tranmission between the motor and the acoustic element.

For the fast acceleration it is important to have an efficient electric motor to get a large force with minimum electric losses. For this purpose it is important to concentrate the magnetic field in a narrow air gap. A solution where the motor is separate from the acoustic part is then simplest because one can individually shape the motor and the acoustic part for optimum performance. It is equally important to keep the mass of moving parts small which is easiest to achieve by using a motor design where the coil is the moving part and a permanent magnet with a narrow airgap is used to generate a strong stationary magnetic field. The coil as the moving part can be obtained with both a linear and a rotary motor.

Figure 2B:
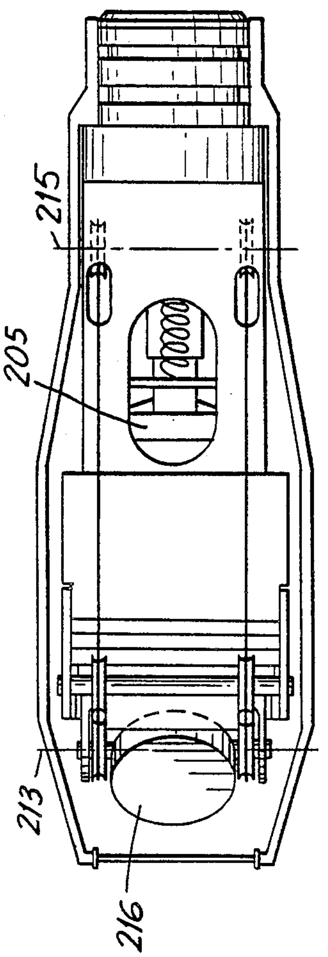
Figure 3:
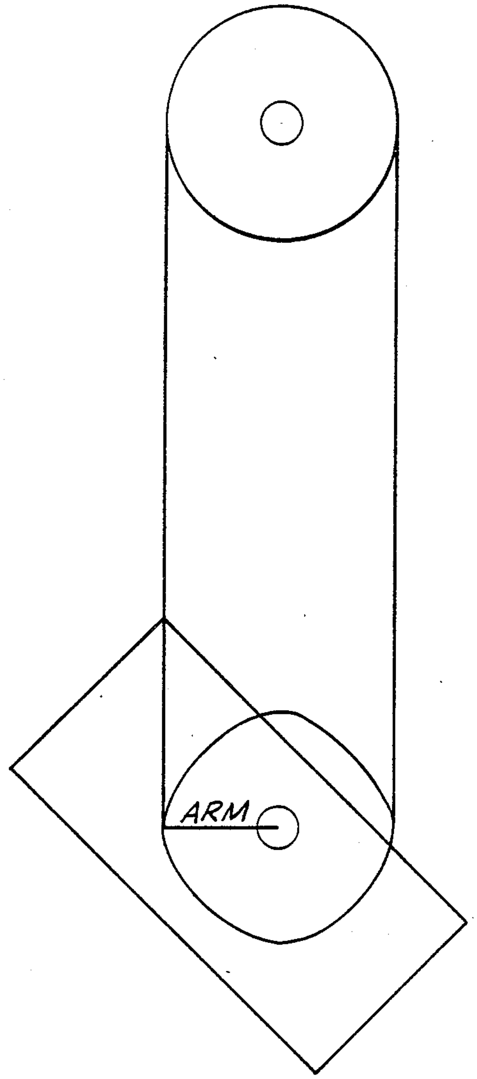
FIG. 3 schematically shows an example of a pulley with angle dependent radius in a particular embodiment of the probe according to the invention.

All these requirements are met with the design illustrated in FIGS. 2*a* and 2*b*. For accelerations, the pulley system has great advantages over other mechanical linkages. The linear motion length, and thereby the mass of moving parts, can be additionally reduced if pulley wheels with angle dependent radii are used, as illustrated in FIG. 3.

The preferred embodiment shall be described with reference to FIGS. 2*a* and 2*b*. In this figure is shown a cylindrical magnet 201 with a magnetic field iron circuit 202. This magnetic circuit generates a strong magnetic field across the airgap 203. In this airgap there is a moving cylindrical electric coil 204 in which we can generate an electromagnetic force along the cylindrical axis by passing a current through the coil in a well known way. This in in the following called the motor coil. The motor coil is mounted to an assembly 205 which is connected to a flexible pulling element 206 by the attachment 207. The coil with the assembly can move linearly through the airgap, guided by the shaft assembly composed of the parts 208, 209, and 210. In this assembly, parts 208 and 210 can be made of a noncritical material, preferably nonmagnetic and nonconducting, while the part 209 is a magnetic material, preferably nonconducting like a ferrite. On the coil assembly 205 is mounted another coil 211, and when the coil assembly is moving, this coil slides in and out over the magnetic material 209. The inductance of this coil will then depend on the position of the coil assembly, and the coil can be used as a simple position sensor. It is in the following referred to as the position coil. By feeding an AC current through the position coil with a defined frequency and amplitude, the voltage over the coil will be proportional to the coil inductance, and thus the position of the coil assembly. The materials in the shaft should be nonconducting to avoid eddy currents induced by the current in the position coil. To avoid magnetic interference between the motor and the position coil, the material in part 208 should also be nonmagnetic.

The pulling element 206 goes around the pulley wheels 212, 214 and 217, which rotates around the shafts 213, 215 and 218. The mounting of all the shafts are not indicated in the figure for simplicity, since they can be arranged in a trivial way. By this the linear motion of the coil assembly is transformed into a rotary motion of the pulley wheels. The acoustic transducers 216 and 219 are connected to the pulley wheels 212 and 217 respectively. The whole assembly is then mounted in a cover 220 filled with a liquid which transmits the ultrasound beams through the front material 221 of the probe. Beam directions in the illustrated angular positions of transducer elements 216 and 217, respectively, are as indicated with arrows 216A and 217A.

As described above, the arm (pulley radius) in the transfer from linear to rotary motion is constant with the pulley system, independent of the angular position of the beam. This makes the linear stroke of the coil smaller for a given opening angle of the sector, compared to using a mechanical linkage rod or arrangement. Since the arm is constant, there is a linear relationship between position of the coil and angular position of the beam. By this it is simpler to use a position sensor for the linear motion of the coil instead of the angular motion of the transducer. One must only make sure that the pulling element is so inelastic that the resonance frequency of the transmission is well above the bandwidth required. By this is a very simple position sensor can be used as shown in FIG. 2*a*. This is an example and other methods of position sensing like bicoil induction can be used.

To maintain the pulley wheel arm when the beam is at the outer directions of the sector, and reduce the linear stroke of the coil, a noncircular pulley wheel where the radius depends on the angle can be used, as illustrated in FIG. 3. Thus, a larger arm is obtained at the outer directions of the sector where a larger momentum is required, and a smaller arm at the more central directions in the sector so that a shorter linear motion is required. By this a shorter coil can be used and the mass of moving parts can be reduced.

Figure 4A:
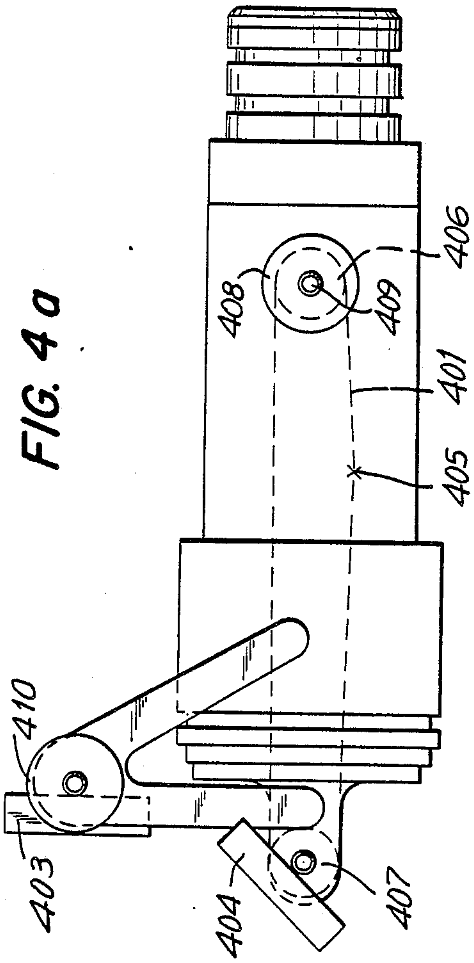
FIGS. 4*a* and 4*b* schematically show a particular embodiment of the probe wherein separate pulling elements are used for the tissue and flow (Doppler) transducers when there is a large difference between the diameters of the tissue and flow transducers.
Figure 4B:
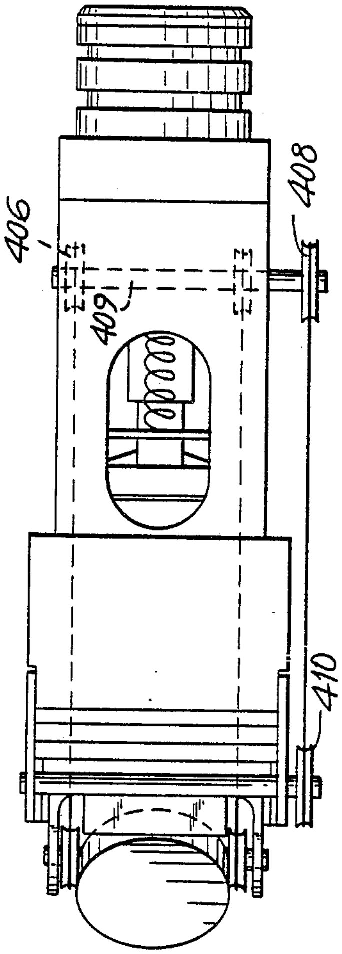

FIGS. 4*a* and 4*b* an embodiment of the probe is shown wherein two separate pulling elements 401 and 402 are used for the flow (Doppler) transducer 404 and the tissue transducer 403. The pulling element for the flow transducer is in this embodiment connected to the motor coil at 405, and thread around the pulleys 406 and 407 so that movement of the flow transducer is obtained. Movement of the tissue transducer is obtained by that the pulley 408 is firmly connected to the upper shaft 409 of the flow pulley system, and thus rotates with the pulley 406 when the motor coil is moving. The pulling element for the tissue transducer is then thread around the pulleys 408 and 410 so that movement of the motor coil causes a pivoting motion of the tissue transducer.

With reference to the drawings, an arrangement of two ultrasonic transducers has been described. If necessary or desired it may be possible to include three or even more transducers, each being associated or rotatable with a separate one of three or more pulleys with a flexible pulling element trained around all the pulleys. In this connection it may be possible to have the pulling element trained around the pulleys in such a way that one or more pulleys and associated transducer(s) have another direction of angular movement than the other pulleys.

In most practical embodiments there will be at least one pulley, such as the pulley 214 in FIGS. 2*a* and 2*b*, which is not associated with any transducer element, and in such cases the motor coil assembly is preferably connected to the pulling element at a portion thereof between such a pulley and another pulley which may be associated with an ultrasonic transducer element.

I claim:

1. An ultrasonic probe for use in combined and time shared ultrasonic imaging of biological tissue structures together with blood velocity measurements and imaging of blood flow based on the Doppler principle, in which rapid changes of sweep movements of the probe between the respective imaging measurement modes of operation are performed, said probe having two mechanically steerable ultrasonic beams, comprising:

a linear motion electric drive motor having a stationary magnet means and a coil assembly which is linearly moveable with respect to said magnet means by the application of electric current to said coil assembly;

two ultrasonic transducers for emitting respective ultrasonic beams and disposed to be pivotable around separate axes within separate angular sectors for sweeping the two ultrasonic beams within the two separate angular sectors, respectively;

mechanical coupling means for connecting the linear drive motor to the pivotable transducer elements, converting the linear motion of the motor coil assembly into a limited rotary motion of the transducers within said angular sectors;

said mechanical coupling means comprising at least three pulleys mounted at a distance from each other, and at least one flexible pulling element trained about and rotatably connecting said at least three pulleys with each other;

said ultrasonic transducers being each rotatably connected to a separate one of the pulleys, and at least one of the pulleys to which one of said transducers is connected having a non-circular circumference with an angle dependent radius; and said motor coil assembly being mechanically connected to said at least one pulling element at a portion thereof lying between two pulleys of said at least three pulleys, whereby reciprocating linear movement of the coil assembly causes said angular sweeping of the transducer elements.

2. An ultrasonic probe according to claim 1, further comprising a position sensor for beam direction, said position sensor having a sensor element connected to and adapted to move with said coil assembly.

3. An ultrasonic probe according to claim 2, in which one of at least one of the pulleys to which said transducers is connected has a non-circular circumference with an angle dependent radius.

4. An ultrasonic probe according to claim 3, in which each of said transducers is mounted to an axle to which one of said pulleys is secured for rotation therewith.

5. An ultrasonic probe according to claim 1, in which each of said transducers is mounted to an axle in which one of said pulleys is secured for rotation therewith.

6. An ultrasonic probe according to claim 1, wherein said motor coil assembly is mechanically connected to said at least one pulling element at a portion thereof lying between one pulley which is associated with an ultrasonic transducer element rotatably connected thereto, and another pulley which is not associated with an ultrasonic transducer element.

7. An ultrasonic probe according to claim 6, wherein there is provided one pulling element which is trained about three pulleys.

8. An ultrasonic probe according to claim 6, wherein there are provided two pulling elements, of which a first pulling element is trained around at least two pulleys to provide for the pivoting of a first transducer, and a second pulling element is trained around at least two other pulleys to provide for the pivoting of a second transducer, said first pulling element being connected to said motor assembly and trained around at least one pulley which is firmly rotatably connected to a second pulley around which said second pulling element is trained to provide pivoting of said second transducer.

9. An ultrasonic probe for use in combined and time-shared modes of ultrasonic imaging of biological tissue structures together with blood velocity measurements and imaging of blood flow based on the Doppler principle, in which rapid changes of sweep movements of the probe between the respective imaging and measurement modes of operation are performed, said probe comprising:

a linear motion electric drive motor having stationary magnet means and coil means selectively linearly movable with respect to said magnet means by the application of an electric current to said coil means;

a plurality of ultrasonic transducer means for emitting a corresponding plurality of ultrasonic beams, each said transducer means being disposed for pivotal movement within a respective angular sector for sweeping the ultrasonic beam across at least a portion of said respective angular sector;

mechanical coupling means connecting said linear drive motor to said plural pivotally mounted transducer means and converting said linear motion of the coil means into a limited rotary motion of said plural transducer means for sweeping said ultrasonic beams within said angular sectors, said coupling means comprising at least three rotatable pulleys mounted in relatively spaced apart relation and at least a flexible pulling element trained about and between said spaced apart pulleys;

each said ultrasonic transducer means being connected to a respective one of said pulleys for rotation therewith; and said motor coil means being mechanically connected to said pulling element at a portion thereof lying between two of said spaced apart pulleys for movement of said coil means with said pulling element so that selected linear movement of said coil means relative to said stationary magnet means by the application of an electric current to said coil means effects steered sweeping of each said ultrasonic beam across at least a portion of the respective angular sector.

10. An ultrasonic probe in accordance with claim 9, further comprising a position sensing means for detecting the angular position of the beam in said angular sector, said position sensing means including a sensor element connected to and adapted for movement with said motor coil means.

11. An ultrasonic probe in accordance with claim 10, said position sensing means further comprising a stationary magnetic means, and said sensor element comprising position coil means movable with said motor coil means along and relative to said stationary magnetic means to thereby vary the inductance of said position coil means in dependence upon the relative positions of said stationary magnetic means and said position coil means.

12. An ultrasonic probe in accordance with claim 10, at least one of said pulleys to which one of said transducer means is connected having a non-circular circumference with an angle dependent radius, and said flexible pulling element being trained about said non-circular circumference of said at least one pulley.

13. An ultrasonic probe in accordance with claim 12, further comprising an axle rotatably supporting one of said pulleys to which one of said transducer means is mounted.

14. An ultrasonic probe in accordance with claim 9, at least one of said pulleys to which one of said transducer means is connected having a non-circular circumference with an angle dependent radius, and said flexible pulling element being trained about said non-circular circumference of said at least one pulley.

15. An ultrasonic probe in accordance with claim 9, further comprising an axle rotatably supporting one of said pulleys to which one of said transducer means is mounted.

* * * * *